United States Patent [19]
Mühlenberg et al.

[11] Patent Number: 5,836,982
[45] Date of Patent: Nov. 17, 1998

[54] SYSTEM AND METHOD OF DATA COMPRESSION AND NON-LINEAR SAMPLING FOR IMPLANTABLE AND BATTERY-POWERED DEVICES

[75] Inventors: Lambert Mühlenberg, Al Landgraaf; Keon Weijand, Ev Hoensbroek, both of Netherlands

[73] Assignee: Medtronic, Inc., Minneapolis, Minn.

[21] Appl. No.: 801,335

[22] Filed: Feb. 19, 1997

[51] Int. Cl.⁶ .............................. A61N 1/36; A61N 1/362; A61B 5/04; A61B 5/0402
[52] U.S. Cl. ................................................. 607/9; 600/515
[58] Field of Search .................. 607/9; 600/515

[56] References Cited

U.S. PATENT DOCUMENTS

| | | | |
|---|---|---|---|
| 4,466,440 | 8/1984 | Money et al. | 607/9 |
| 4,503,510 | 3/1985 | Weaver . | |
| 4,567,883 | 2/1986 | Langer et al. . | |
| 4,633,884 | 1/1987 | Imai et al. . | |
| 4,716,903 | 1/1988 | Hansen et al. | 607/9 |
| 4,920,489 | 4/1990 | Hubel Bank et al. | 600/515 |
| 5,215,098 | 6/1993 | Steinhaus et al. . | |
| 5,217,021 | 6/1993 | Steinhaus et al. . | |
| 5,255,186 | 10/1993 | Steinhaus et al. . | |
| 5,263,486 | 11/1993 | Jeffreys . | |
| 5,312,446 | 5/1994 | Holschbach et al. . | |
| 5,543,795 | 8/1996 | Fernald . | |
| 5,603,331 | 2/1997 | Heemels et al. | 607/25 |

FOREIGN PATENT DOCUMENTS

0 583 490 A1  2/1994  European Pat. Off. .

Primary Examiner—William E. Kramm
Assistant Examiner—Carl H. Layno
Attorney, Agent, or Firm—Michael J. Jaro; Harold Patton

[57] ABSTRACT

A system and method of non-linear sampling of an analog signal, and for data compression, to provide overall compressed digital representative of analog signal such as a physiological signal obtained in a battery powered device such as an implantable pacemaker. Non-linear sampling is provided by generating a time varying threshold signal against which the analog signal is compared every clock sample, with the sample being skipped if the input analog signal does not exceed the threshold signal. The threshold signal can be either analog or a plurality of discrete levels, enabling up to a predetermined maximum number of samples to be skipped. The non-linearly sampled data is further compressed, using lossless techniques for compressing both the amplitude data and the data representative of skipped samples, to provide data for decompression. In a specific pacemaker embodiment, the data compression system recognizing a marker channel event, and includes data representative of the time and type of marker channel event.

24 Claims, 6 Drawing Sheets

SYSTEM AND METHOD OF DATA COMPRESSION AND NON-LINEAR SAMPLING FOR IMPLANTABLE AND BATTERY-POWERED DEVICES

FIELD OF THE INVENTION

This invention relates to systems for compressing and sampling analog signals, and in particular physiologic signals such as cardiac signals, so as to achieve efficient data compression with relatively little data loss, and with a minimum of data processing.

BACKGROUND OF THE INVENTION

As a result of significant technological growth over the past decade, implantable, battery-powered devices can now be equipped with processing circuitry and memories for storing episodes of digitized physiological signals. For example, a pacemaker may be designed to perform the task of sensing, digitizing and storing intracardiac signals for later uploading to an external device. The pacemaker system need not be restricted to acquiring cardiac signals, but can also be used for obtaining, digitizing, and storing sensor signals, e.g., pressure sensor signals. Such signals are conventionally continuously sampled at a high rate in order to capture the anticipated high amplitude and high frequency components, such as those which occur during the actual contraction of the heart. Examples of systems already in use which obtain and store digitized physiological signals are pacemaker-cardioverter-defibrillator units (PCD's) and implantable hemodynamic monitors.

In such systems, and particularly implantable battery-driven systems, the task of digitizing the data for storage and transmission to an external receiver becomes difficult because of the need to conserve data processing time, which in turn consumes significant power. Generally available memory is a limitation, but even where the memory limitation is not significant, some sort of data compression scheme is suggested in order to save power during the data processing and telemetry steps. It is known that data compression techniques can be used in order to increase the amount of signal information available for storage in available memory. See pending U.S. applicatlion Ser. No. 08/561,738, P-3432, "System and Method for Compressing Digitized Signals in Implantable and Battery-Powered Devices," filed Nov. 22, 1995.

Because of the limited availability of processing resources and battery power, compression techniques for such implantable systems need to focus on achieving the greatest degree of data compression which is consistent with allowable loss of information. Thus, some lossy compression can be utilized in these environments, for achieving higher compression ratios at the expense of some signal distortion.

In view of the above background, the system and method of this invention provide improvements over the prior art method of lossless compression of digitized physiological signals, which method typically achieves about a 2:1 compression ratio. This method can be enhanced to achieved higher compression ratios at the expense of some signal distortion, i.e., by a form of lossy compression. The basic idea behind the lossy compression method of the technique of this invention is to allow for some minimal signal distortion with regard to those portions of the signal which are least interesting, i.e., contain the least amount of information, while minimizing distortion during the more interesting portions such as the actual QRS complex. The net result of such an enhanced technique is a signal where, depending on the signal activity, samples of the signal during the less interesting portions are discarded, such that the sample intervals are not constant. In this form of non-linear sampling, the accepted samples, which represent the signal during the more data-intensive portions, can be stored with the original-lossless technique, such that the signal can be exactly reproduced for those moments and portions where the samples are available.

Additionally, the system of this invention goes on to provide, for the pacemaker environment, a technique for merging pacemaker markers into the compressed data stream, to obtain an annotated compressed signal.

In a further aspect of this invention, there is provided a system and technique for non-linear sampling which is carried out by hardware before the actual digital sampling and A/D conversion. As discussed below in relation to the preferred embodiments, a good quality ECG or EGM signal can be obtained with only 20–25% of the samples required in a conventional system where no samples are discarded. This not only reduces the amount of data that needs to be stored, but saves battery power, since the implanted device only needs to process, or operate on an average of, e.g., about 50 samples rather than 200 samples per second. Following such non-linear sampling, and after A/D conversion, there is provided a post-processing technique for further compression of the data produced by the non-linear sampling A/D converter.

SUMMARY OF THE INVENTION

It is an object of this invention to provide a system usable in an implantable and battery powered device, or other device with limited power, for improved sampling and compression of data so as to provide an optimized tradeoff between the compression ratio and signal loss, so as to optimize the system capacity to digitize and store signals.

In view of the above overall object, there is provided an improved system which encompasses improvements both in sampling and in data compression. A minimally lossy non-linear sampling technique is provided for skipping samples representative of portions of the input signal which contain little data, and for providing maximum sampling during data-significant portions of the signal so as to minimize distortion. This technique of non-linear sampling provides a reduced effective sample rate. The samples that are obtained are subjected to linear compression, whereby the combination of non-linear sampling and linear compression enables a substantial overall savings in data processing and storage requirements.

In accordance with one embodiment of this invention, non-linear sampling can be carried out after initial sampling and A to D conversion, to achieve effective data compression through discarding of low information samples. In another preferred embodiment, non-linear sampling is carried out before A/D conversion, providing further savings in the power required for data processing. The digital data representing the accepted samples is combined with data representing the skipped samples, both groups of data being linearly compressed so that the signal can be decompressed and reconstructed, subject to the minimal loss resulting from skipped samples.

In another feature of the system of this invention, applicable specifically to an implantable pacemaker, marker channel information representing pacemaker events such as generated pace pulses is obtained and interspersed with sample data for compression and storage.

DESCRIPTION OF THE PREFERRED EMBODIMENTS

Figures 1A, 1B:
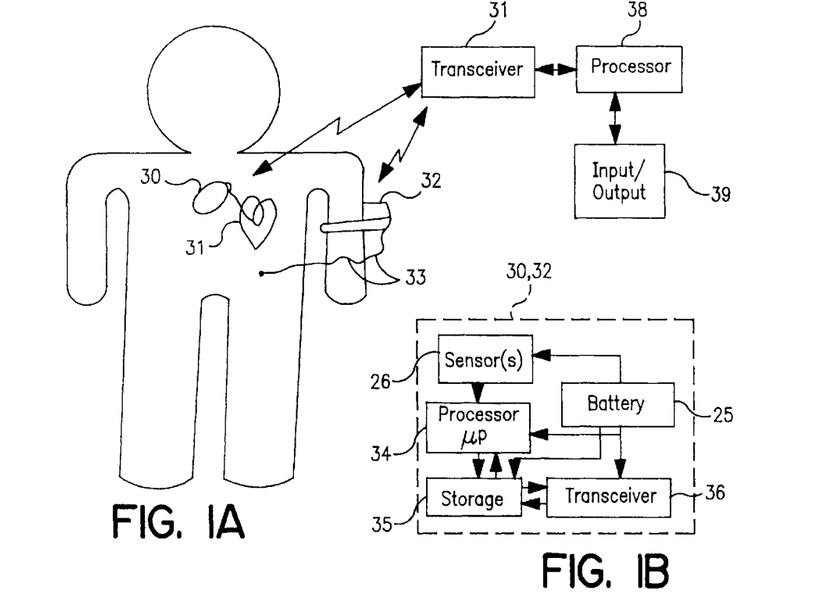
FIG. 1A is diagram representing two exemplary forms of devices to which the invention is applicable, namely an implanted device such as a pacemaker, and a battery-powered holter-device worn on the outside of a patient.
FIG. 1B is a simple block diagram representing the major elements of an implantable or wearable device such as illustrated in FIG. 1A.

Referring now to FIG. 1A, a diagram is shown illustrating the environment of the apparatus and method of this invention. The invention may: be used with an implantable device such as a pacemaker 30, illustrated as implanted within a patient. Connected to the pacemaker is a lead 31, which extends into the patient heart, and has one or more electrodes at the distal end thereof which deliver stimulus pulses and also sense intracardiac or epicardial signals. As is well known in the pacemaker art, the sense signals can be received by the pacemaker, digitized and stored in memory, for later transmission to an external device 37; alternately, they can be down-loaded directly to an external programmer device. Likewise, one or more sensors located on the lead or in the pacemaker can produce the signals which are to be digitized and stored. As shown, the transceiver 37 may be a conventional programmer as used in the pacemaker art. The programmer, when it has received data from the pacemaker, can transfer it to a processor 38, which in turn can output data to input/output device 39, all in a well known manner. As is well known, implantable devices such as pacemakers have been limited in their capacity to handle vast amounts of data, because of obvious limitations on power and memory capacity.

Also illustrated in FIG. 1A is a wearable device 32, shown strapped to the arm of a patient. Such device 32 may operate in conjunction, for example, with electrodes 33, for determining a patient ECG. As with the implanted device, data collected in battery powered device 32 can be downloaded to another device for further processing and outputting. Similar restrictions on processing and memory availability may apply to such a battery powered wearable device. Although two types of devices are illustrated in FIG. 1A, the invention is not limited to any specific class of devices.

Referring now to FIG. 1B, there is shown a simple block diagram representing the major elements of an implantable or wearable device 30,32 in accordance with this invention.

A battery 25 powers a sensor or sensors 26, which include leads 31 or 33. The sensor block may also include an amplifier stage and digitizing circuitry of conventional form. The digitized data is transmitted to processor block 34, which suitably contains a microprocessor. It is to be understood that the processing steps encompassed in this invention may be undertaken with any desired combination of dedicated hardware and/or software. The microprocessor is in communication with memory or storage, as shown at 35; the memory in turn is in communication with transceiver 36, for transmitting data to outside apparatus or receiving data and/or instructions therefrom.

Figure 2:
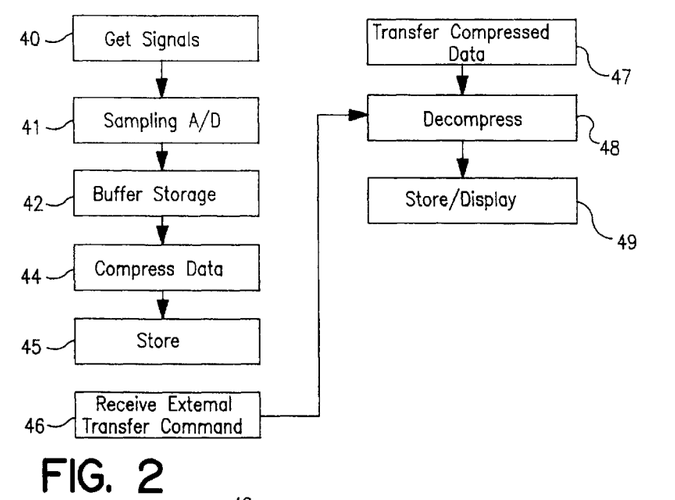
FIG. 2 is a simple flow diagram representing the major steps taken in compressing, transferring and decompressing data in accordance with this invention.

Referring now to FIG. 2, there is shown a simple flow diagram representing the major steps taken in compressing, transferring and decompressing data in accordance with this invention. At 40, the signals, suitably physiologic signals such as EKG signals, are picked up in analog form. The analog signals are sampled and converted from analog to digital data at 41. As discussed below, this may involve A/D conversion followed by removal of certain samples to provide effective non-linear sampling; or skipping of certain samples before A/D conversion. The digital data is stored in buffer storage as shown at 42. At block 44, the data is compressed in accordance with one of the techniques of this invention, and stored at block 45. At 46, a command to transfer data is received from an external source, indicating the availability to receive stored data. The compressed data is transferred at 47, in a conventional manner as is well known in the pacemaker art. At 48, the data is decompressed at the external device, to recreate the original signals in digital form. The signal data is then stored at 49, or displayed.

Figure 3:
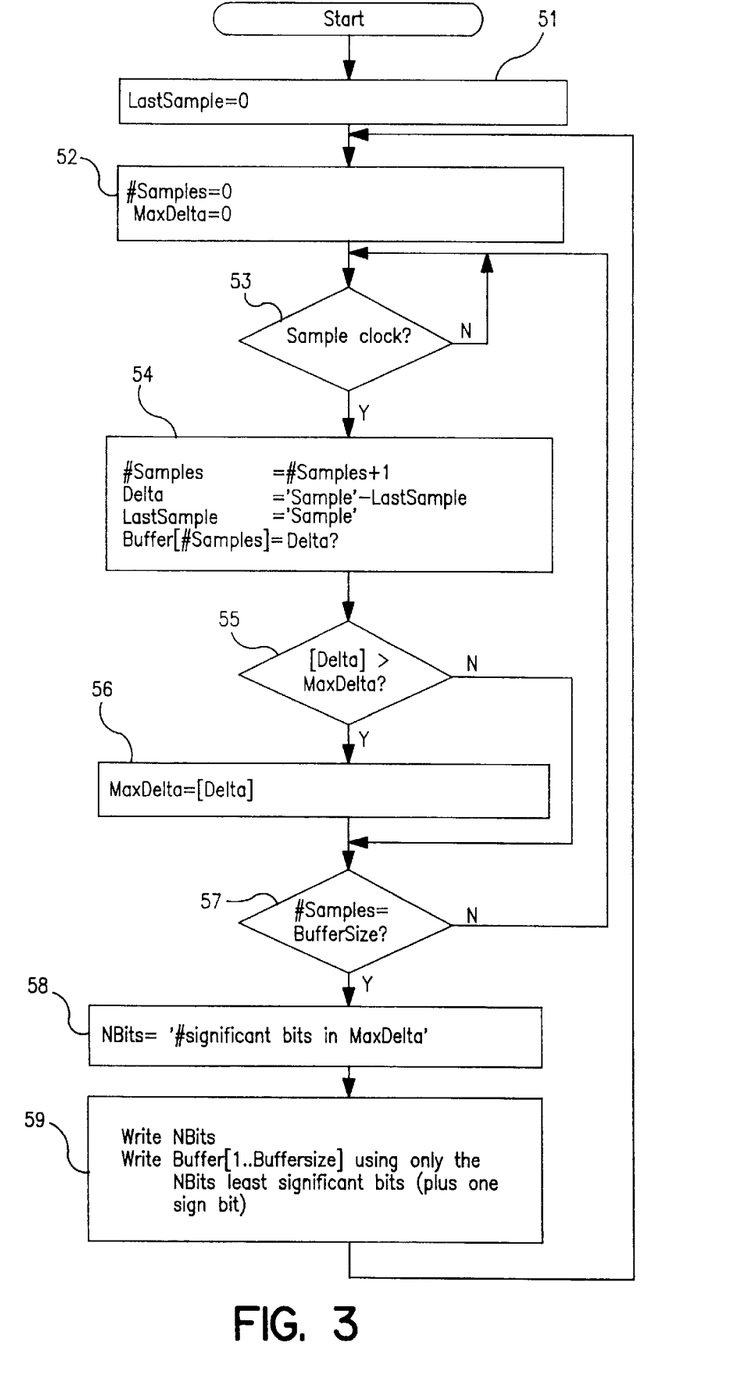
FIG. 3 is a flow diagram of a prior art embodiment of the technique for lossless compression of data.

Referring now to FIG. 3, there is shown a flow diagram of steps taken in accordance with prior art application Ser. No. 08/561,738 for achieving lossless compression. Typically, this technique achieves about a 2:1 compression ratio, and requires only a minimal amount of data processing, thereby making it suitable for use in implantable or other devices having limited power supplies. The raw technique of the algorithm is to store the deltas, or differences in value (magnitude and sign) between successive individual samples with a minimum number of bits. Because the value of a sample number zero is unknown, it is assumed to be a value corresponding to a 0 volt input signal, and is also the integration constant that is to be used during signal construction. Accordingly, as indicated at 51, the variable LastSample is set equal to zero. Blocks 51–57 form a loop in which a block of deltas is assembled, the optimal size of a block being between 5 and 12 samples. At block 52, the variable #Samples is set equal to zero and the variable MaxDelta is set equal to zero. At 53, the routine waits for a sample clock, the clocks being generated at a predetermined fixed rate. When a clock is received, the operations indicated at block 54 are carried out, with the delta value being stored in a buffer corresponding to the current sample number designated #Samples. Next, at 55, it is determined whether the absolute value of delta is greater than the presently stored MaxDelta. If yes, then MaxDelta is reset to such absolute value, and otherwise the routine does not change MaxDelta. At 57, it is determined whether the variable #Samples equals the BufferSize, i.e., have all of the samples for this block of data been examined? If no, the routine loops back to 53 and continues. When the answer at 57 is yes, at 58 the routines determines NBits, which represents the number of significant bits in MaxDelta, e.g. 3 or 4 bits. Determining the NBits parameter can be done either in hardware with the priority encoder, or with software by counting the number of right shifts until MaxDelta reaches a zero value. Following this, at step 59, the block of data is written into the device's main signal storage memory by first writing the number of significant bits as a block header and then writing all assembled deltas by writing only the NBits least significant bits, plus one sign bit indicating a positive or negative delta.

Analysis of five sample cardiac signals which have been processed using this compression method indicates that all five of the signals compressed at better than a 2:1 average, with an average compression of about 55%. Reconstruction of the signal is also done on a block-by-block basis, as disclosed more fully in Ser. No. 08/561,738. First the value of NBits is read, and next all deltas within the block are reconstructed by reading the N least significant bits plus the sign bit. Adding the deltas to the previous sample value finally leads to the original signal.

Figure 4:
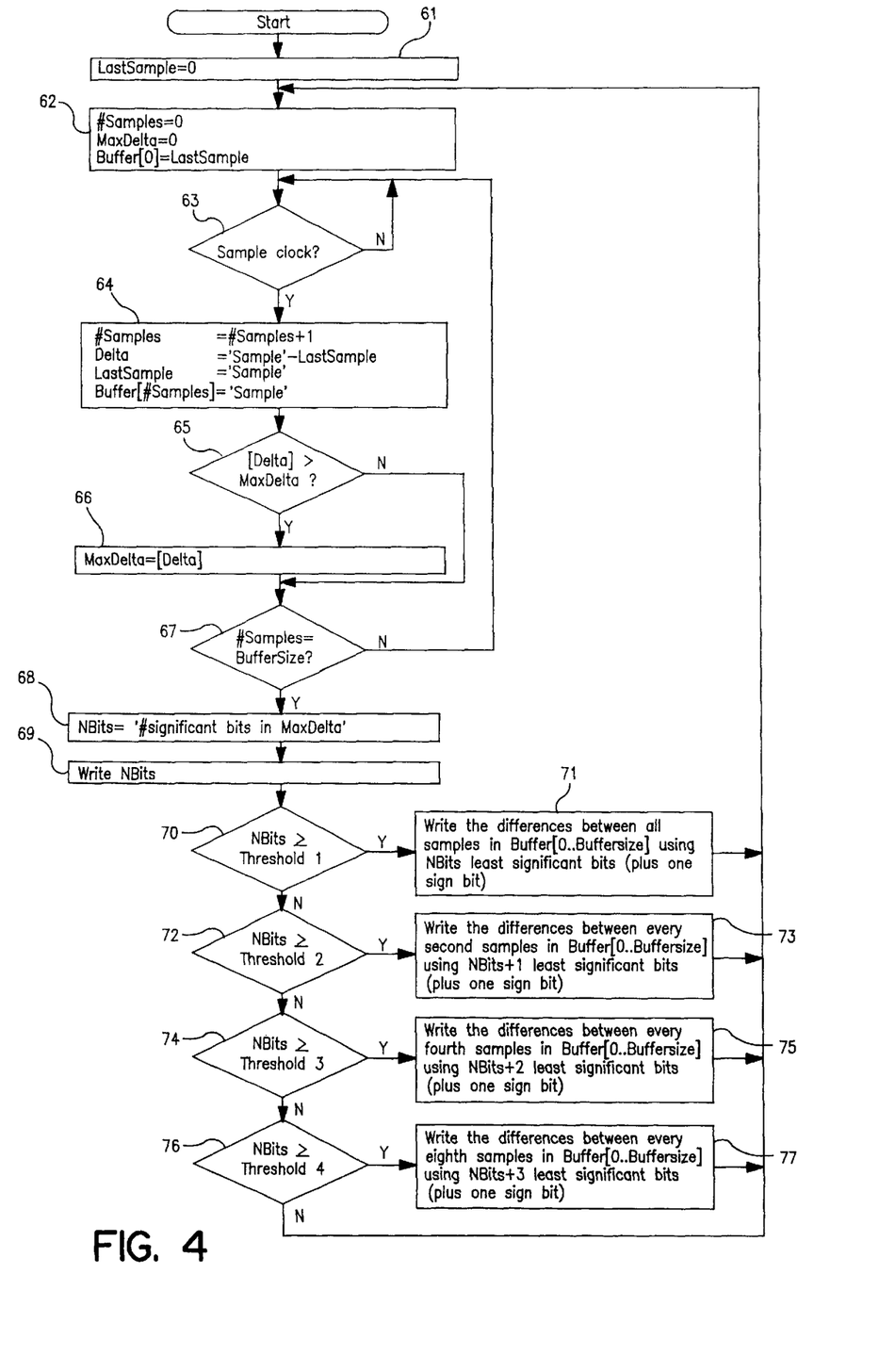
FIG. 4 is a flow diagram of an algorithm for lossy compression, based on non-linear sampling as a function of predetermined thresholds.

Referring now to FIG. 4, there is shown a lossy compression algorithm for achieving a higher compression ratio as compared to the lossless compression algorithm of FIG. 3. Experiments have shown that more sophisticated lossless signal compression techniques, as compared to the technique of FIG. 3, achieve only about an additional 10% compression, but do so at the expense of significantly more processing and memory resources. Significantly higher compression ratios can be achieved only when some distortion of the reconstructed signal is allowed. The distortion should, however, be minimized to guarantee that the reconstructed signal is still clinically relevant. Physiological signals, such as ECG, are usually sampled at a relatively high rate to ensure correct capture of the fastest components. A respiratory signal is sampled at a high rate to capture the signal correctly during exercise, but the sample rate can be lowered during rest or sleep. Cardiac signals are sampled at a minimal rate of 200 Hz to capture the QRS complex; the P- and T-waves can be sampled at a lower rate, since they are relatively more spread out, while the sample rate can be lowered even further between the complexes without losing much information. Using this insight, it is seen that it is possible to enhance the lossless compression method with an algorithm that adapts the effective sampling rate per data block depending on the signal activity in that block. Thus, the lower the signal activity within a block, the more samples can and will be discarded; while for blocks with high signal activity, little or no samples are discarded. The result is a lossy compression method with minimal distortion of the high activity portions of the analog signal.

Referring now to the flow chart of FIG. 4, it is seen that the first part of the algorithm, i.e., the acquisition of a block of samples and the storing of data representing delta values for the samples, as carried out at blocks 61–69 inclusive, is nearly the same as in the algorithm of FIG. 3. However here, while the MaxDelta is again determined for the block, the actual sample values, instead of the delta values, are stored in the buffer, as seen at blocks 62 and 64. Otherwise, steps 61–68 correspond to steps 51–58 of FIG. 3. At block 69, NBits is again written, and then the compressed data is determined according to the steps indicated at 71–77. Here, the parameter NBits is used as a measure of the degree of signal activity within the block. Four threshold values of NBits are stored, as indicated at blocks 70, 72, 74 and 76. The number of samples for which the data is stored depends upon how the parameter NBits compares with the four threshold values. Thus, at block 70, if NBits is larger than a first highest threshold value, the routine goes to block 71 and writes all deltas in the same manner as in the lossless algorithm of FIG. 3. However, if NBits is not greater than threshold 1, the algorithm goes to 72 and compares the parameter to threshold 2, which is less than threshold 1. If NBits is greater than threshold 2, then the deltas between every second sample are stored. Since this delta difference can possibly be as great as 2*MaxDelta, these delta differences must be written with NBits+1 least significant bits. If NBits is lower than this second threshold, it is again checked against a third and even lower threshold, as seen at 74. If the signal activity is high enough that Nbits is greater than threshold 3, the differences between every fourth sample are stored, now using NBits+2 least significant bits, since the maximum effective delta may be as great as 4*MaxDelta. If NBits is still lower, it is compared to the lowest threshold 4, at block 16, to be determined if the deltas between every eighth sample can be stored, or whether there is no sample value stored at all. If the differences between every eighth sample are stored, as indicated at block 77, this value is written using NBits+3 least significant bits. In each case, an additional bit is written to indicate whether the delta is plus or minus. Following writing of the samples in the buffer, the routine returns to block 62, and commences to loop through again, processing the next block of data.

It is to be noted that the algorithm of FIG. 4 places a constraint on block size, which should be a multiple of 8. During decompression, the flow diagram of which is not shown, the decompression routine compares the written NBits with the known thresholds, and thereby determines the number of bits used in writing the sample differences, or deltas. The discarded samples can be reconstructed with interpolation techniques. An analysis of the compression results derived from applying this lossy compression technique to four different cardiac signals indicated compression ratios in the range of about 3.5:1 to 5.5:1, the higher threshold settings providing the higher compression ratios.

Figure 5:
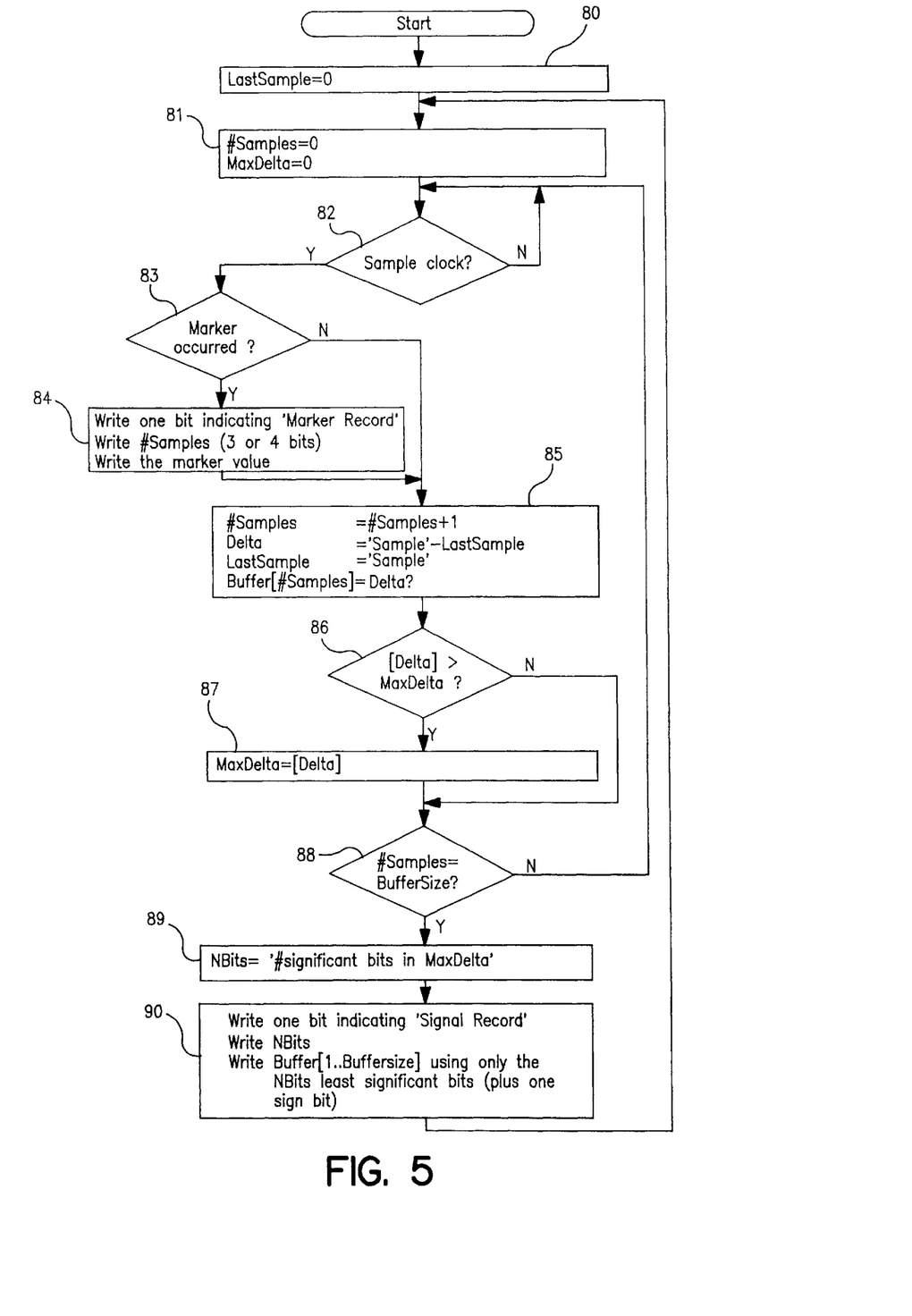
FIG. 5 is a flow diagram of an algorithm for adding pacemaker marker channel data to a data stream which is then compressed in accordance with this invention.

Referring now to FIG. 5, there is shown a flow diagram of a further algorithm designed to add a pacemaker's marker channel to the compressed signal. This algorithm is applicable to both the lossless and the lossy compression methods. As seen in FIG. 5, the only additional steps compared to the lossless routine are those presented at blocks 83 and 84, as well as the step at block 90 of writing a signal bit indicating that the signal record is following. Thus, steps 80–82 are preparatory to obtaining sample data. At 83, the pacemaker determines whether a marker has occurred. Thus, immediately following a sample clock, a check is made by the pacemaker to determine if a marker has been generated. If not, the new sample clock is processed in the same way, as seen at blocks 85–89. However, if a mark has occurred, data is written at block 84. Note that this data concerning the marker record is written during the acquisition phase when deltas are being determined, and before writing of all of the block data, which is done at 90.

Referring specifically to step 84, when a marker has occurred, a single bit, i.e., a binary 1, is written indicating "marker record." Following this, the value of NSamples, either 3 or 4 bits, is written, providing information as to where in the block the marker record was received. This preserves a record of where, within the physiologic signal, the marker occurred. After this, the marker value is written, providing data concerning the actual marker.

After the entire buffer has been analyzed, at block 90 the algorithm causes the writing of another bit, i.e., a binary 0, to indicate that the actual signal record now follows. After this, NBits is written, and the buffer is written to contain the delta information, as discussed previously. Note that if a block includes a marker record, the block data starts out with the data written at block 84, followed by the bit indicating signal record, and then the data describing the block. If no marker has occurred during the block, then the only change is that the block data is preceded by the single bit indicating a signal record. Adding the marker channel data to the compressed signal results in a slight decrease in the compression ratio due to the addition of the record indicator, which is the price paid for adding the additional marker channel data.

Figure 6A:
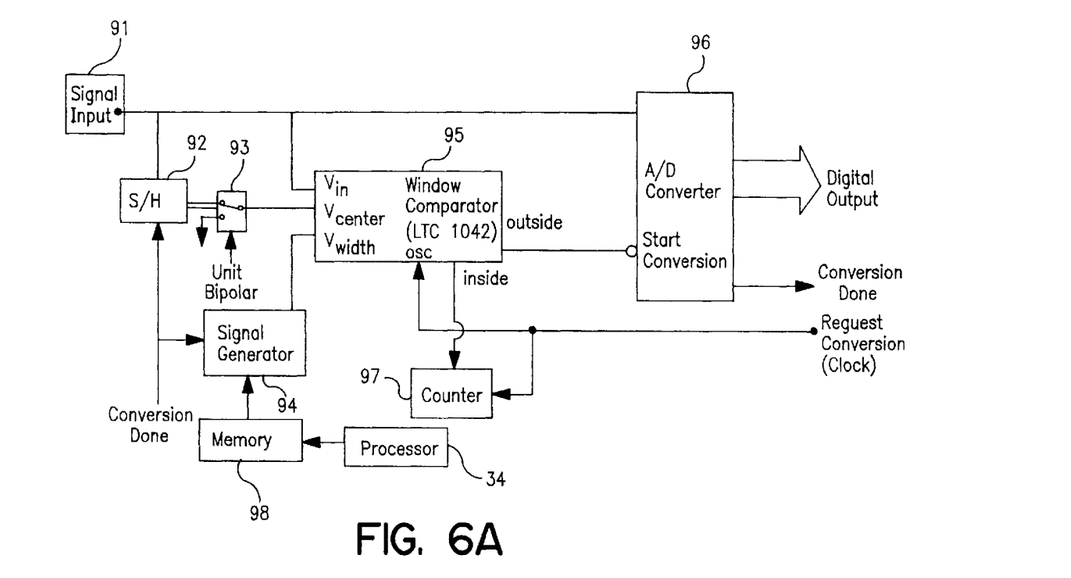
FIG. 6A is a circuit diagram of an analog implementation of apparatus for non-linear sampling and A/D conversion.

Referring now to FIG. 6A, there is shown a preferred embodiment of non-linear sampling prior to A/D conversion. As indicated above in connection with the embodiment of FIG. 4, physiologic signals can be digitized with fewer samples than the sample rate being utilized, if the effective sample rate is dependent upon the momentary signal activity. Thus, good quality ECG and EGM signals can be produced with an average rate of about 50 samples per second as contrasted to the given sample rate of 200. If the decision as to whether or not to discard samples is done before the A/D converter, this can result in a substantial reduction in battery power drain. Such non-linear sampling before A/D conversion both saves power and reduces the amount of data which needs to be stored or processed. It is to be noted that non-linear, as used in this context, means non-linearity in the sample interval time, and does not refer to and should not be confused with any non-linearity in the A/D converter resolution.

Referring to FIG. 6A, the input signal, indicated as coming from a source. at 91, is connected directly to A/D converter 96, for digitizing, but converter 96 is only enabled after an examination of the signal to see whether the change in the signal from the time of the last sample is sufficiently significant. Thus, the sample clock, which is introduced at the input terminal designated "request conversion," is not connected directly to converter 96, but is only gated through when a determination has been made that there is sufficient change in the input signal to warrant a sample. The decision to skip or accept the sample depends on the difference between the signal input and the signal stored in sample and hold circuit 92, which difference is compared to the output signal from signal generator 94. Circuit 92 holds the analog value of the last actually converted sample, and is used as the center value of the input to window comparator 95. The output of circuit 92 is transferred through switch 93 to provide one input to the comparator 95. The second input, designated $V_{in}$, is the analog signal input. A third input is provided from the signal generator. A "conversion done" signal, provided upon conversion of a last sample, is connected both to S/H circuit 92 and signal generator 94. Thus, following conversion of a sample, the Sample/Hold circuit holds the just converted value; the signal generator initiates a threshold signal which starts at a predetermined level and then decreases to zero in time, and is also connected to an input of circuit 95. The window signal from generator 94 is essentially a time varying threshold signal, an analog version of the discreet threshold values utilized in the algorithm of FIG. 4. Circuit 95 compares the threshold signal to the input difference signal, and only when the input difference signal has a value greater than the threshold signal, is the sample clock signal gated through to the start conversion terminal of converter 96. Thus, the longer it takes for the signal generator output to decay to value less than the absolute value of the analog signal as centered around the last sample, the more clock signals are skipped. Only when the signal input difference value is outside of the threshold, or window value, is the sample clock accepted, thereby initiating conversion, at converter 96. When conversion is done, the signal from 91 is converted with the usual resolution, and the digital output is obtained. At this time also, a conversion done signal is generated, which resets signal generator 94, and triggers S/H circuit 92 to update to the latest signal value.

Figure 6B:
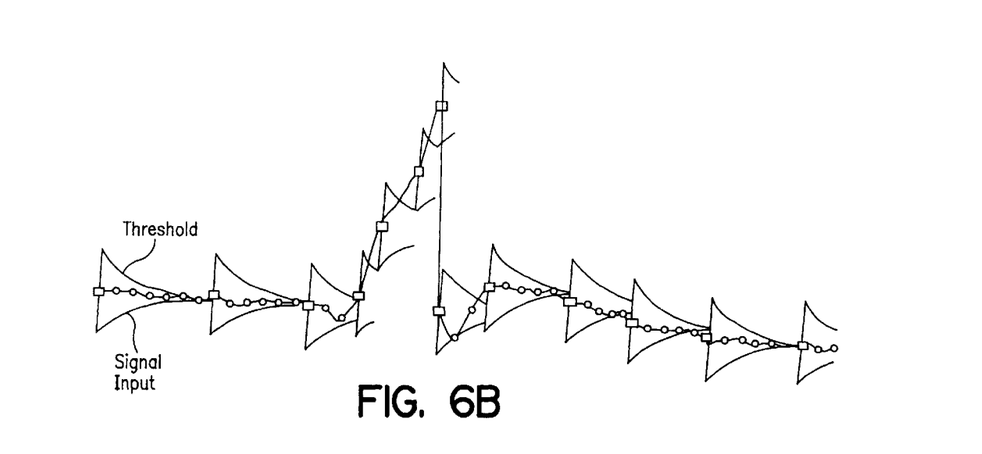
FIG. 6B is a diagram illustrating the operation of the non-linear sampling A/D converter of FIG. 6A.

The operation of the threshold window, or envelope is relation to a varying input signal is seen in the diagram of FIG. 6B. At the time that a sample is taken, indicated by a □ symbol, the signal generator commences a signal providing a two-phase window, i.e., having a plus and minus envelope against which the input signal is compared. As illustrated, the window signal starts at a given value, and decays to zero. Note that the window signal is centered about the last value of the analog signal. For a pacemaker operation, when the input signal is bipolar and the base sample frequency is rather low, e.g., 200 Hz, it has been determined that the circuit performance improves if the comparison window is centered around 0 volts, rather than the previously converted value. For these cases, the analog switch as indicated at 93, is provided to force the center value to 0 volts. Still referring to FIG. 6B, after the first indicated actual sample, there follow six sample clocks, indicated by the ○ symbol, at which the input signal has varied so little compared to the last sample value that it remains within the window, and these samples are skipped. At the time of the seventh sample clock following the last sample, the threshold window, or envelope has decreased to such a minimal value that the signal input is greater than the window, and a start conversion signal is transferred from comparator 94 to converter 96. It is important that the threshold signal decrease to zero within a predetermined number of samples, to ensure that samples are taken at least a minimal sampling rate. As can further be seen in examination of FIG. 6B, when the signal becomes active, the sampling rate increases substantially, reaching the point where the signal is actually sampled on successive sample clocks. Thus, a non-linearity of actual sampling is achieved, adapting the effective sample rate to the relative information content of the physiologic signal.

As can be seen from FIG. 6B, the initial 47 samples have been reduced to 13 samples, a reduction of 72%. Within the QRS complex, however, most samples are accepted, and the sample rate is high enough to provide essentially lossless sampling. Of course, the reduction in the number of samples, and thus the distortion of the reconstructed signal, depends upon the shape of the threshold, or window signal. Accordingly, the shape and timeout of the window signal is a matter of design choice, and is suitably adapted to the nature of the signal being sampled, e.g., a specific physiological signal being obtained. Accordingly, the tradeoff between signal distortion and power/data reduction can be done here solely by the threshold signal generator 94.

Figure 6C:
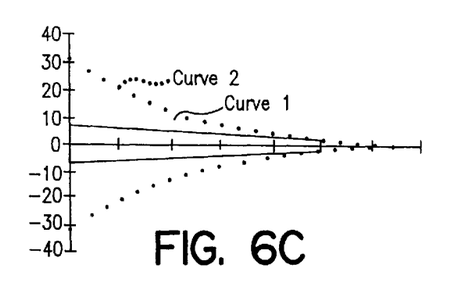
FIG. 6C is an illustration of different threshold curves as can be used in the non-linear A/D converter of FIG. 6A.

To illustrate the effect of threshold signal settings, there are shown in FIG. 6C curves representing two different threshold signals, each of which decay from a starting value to zero in seven clock cycles. The following table indicates the number of skipped samples corresponding to the threshold value for two curves, designated curve 1 and curve 2:

TABLE 1

| # Skipped Samples | Threshold Value | |
| --- | --- | --- |
| | Curve 1 | Curve 2 |
| 0 | 7 | 32 |
| 1 | 6 | 20 |
| 2 | 5 | 12 |
| 3 | 4 | 7 |

TABLE 1-continued

| # Skipped Samples | Threshold Value | |
|---|---|---|
| | Curve 1 | Curve 2 |
| 4 | 3 | 4 |
| 5 | 2 | 2 |
| 6 | 1 | 1 |
| 7 | 0 | 0 |

It is desirable, in a device such as a pacemaker, to be able to vary the threshold window signal in accordance with the circumstances. This is accomplished either by programming or by adjustment based on accumulated data. For example, during periods where a signal is of less amplitude, the initial value of the threshold can be lowered to compensate for what could otherwise be a small increase in distortion. Referring to FIG. 6A, parameter values for the signal generator are stored in memory 98, e.g., initial threshold value; rate of decay; and the maximum number of skipped beats. This threshold parameter data is supplied through processor 34. The parameter data may be supplied by an external programmer, through transceiver 36; or, the microprocessor is programmed to monitor the signal data and, based on signal history as represented by accumulated signal data, make logical decisions concerning optimization of the threshold curve. Such adjustment of the threshold curve can be made either for the analog embodiment as illustrated, or for a corresponding digital embodiment.

The non-linear sampling A/D converter circuit of FIG. 6A can be used directly in a pacemaker for real-time analog uplink telemetry. The sample values are uplinked to the programmer and the discarded samples can be reconstructed within the programmer, using interpolation techniques before the signal is displayed to the user. This overall technique saves substantial power both in the A/D converter and in the uplink telemetry circuit. While the preferred embodiment of an analog non-linear sampling A/D converter has been illustrated, it is noted that an equivalent digital converter is within the scope of the invention.

If a non-linear sample circuit is used for storage of data in the pacemaker, or for further processing, both the sample amplitude value and the interval time need to be taken into account. For this purpose, where the signal input remains inside the window, skipped clock pulses are outputted from comparator circuit 95 to counter 97, thereby providing a record of the number of skipped samples. Accurate storage of the data requires combining the digital data corresponding to the samples amplitude, along with this counter information. If the threshold signal is set such that the maximum number of skipped samples is 7, this means that an 8-bit A/D converted value becomes an 11-bit word, consisting of the 8-bit amplitude value and a 3-bit number indicating the lapsed time, or number of skipped clocks since the last sample. Even though this means an overhead of 3 bits per accepted sample, the overall result is less memory needed for signal storage, as well as a reduction in battery power drain.

The stream of 11-bit sample words that is generated by the circuit of FIG. 6A, as described above, can be compressed further using a combination of the lossless compression technique for the amplitude value and a fixed Huffman coding for the lapsed time. A distribution of the number of skipped samples, or lapsed time, for different non-linear sampled physiological signals, indicates that there is no strong correlation or similarity of such distribution between different sample signals. This implies that direct compression of the number of skipped samples is difficult. However, when one examines the differences (or deltas) between the number of skipped samples for successive sample pairs, it is seen that there is a strong correlation for the deltas between the number of skipped samples for different signals, indicating that delta (# skipped samples) is a parameter that can be compressed. The disadvantage with this parameter, however, is that the range of different values runs from −7 to +7, which would mean that 4 instead of 3 bits are need to store this delta value, as opposed to storing simply the parameter # skipped samples. However, if the delta value modulo 8 is used, the range is changed back to 0–7, by which the individual number of skipped samples can still be reconstructed. This change means only that the negative delta values are changed into a positive number by the formula "8—absolute value of delta". Thus, if the number of skipped samples changes from 6 to 3 (delta =−3), the same result can be obtained if a delta of +5 is used:

(6+5)*MOD* 8=11 *MOD* 8=3.

It has been found that there is still a strong correlation for this final parameter delta( # skipped samples) modulo 8. Accordingly, this distribution is a the basis for developing a fixed Huffman code for a more efficient representation of the time lapsed, or skipped samples parameter. The techniques for creating a Huffman code tree from a probability distribution are described in the literature. For physiological signals sampled with the threshold signals as set forth in Table 1 and FIG. 6C, a distribution of delta (# skipped samples) modulo 8 can be determined, from which as a result a Huffman coded tree can be obtained with the resulting codes for the different values:

TABLE 2

| 0 | 1 |
|---|---|
| 1 | 000 |
| 2 | 0101 |
| 3 | 01101 |
| 4 | 01100 |
| 5 | 0111 |
| 6 | 0100 |
| 7 | 001 |

Using this Huffman coding results in a reduction of about 17.5% bits for the first threshold setting, and about 14.5% reduction of bits for the second threshold setting. Since a fixed Huffman code is used, implementation of this coding is a matter of finding the corresponding code for each parameter in a very small look-up table, such that there is hardly any processing involved.

Figure 7:
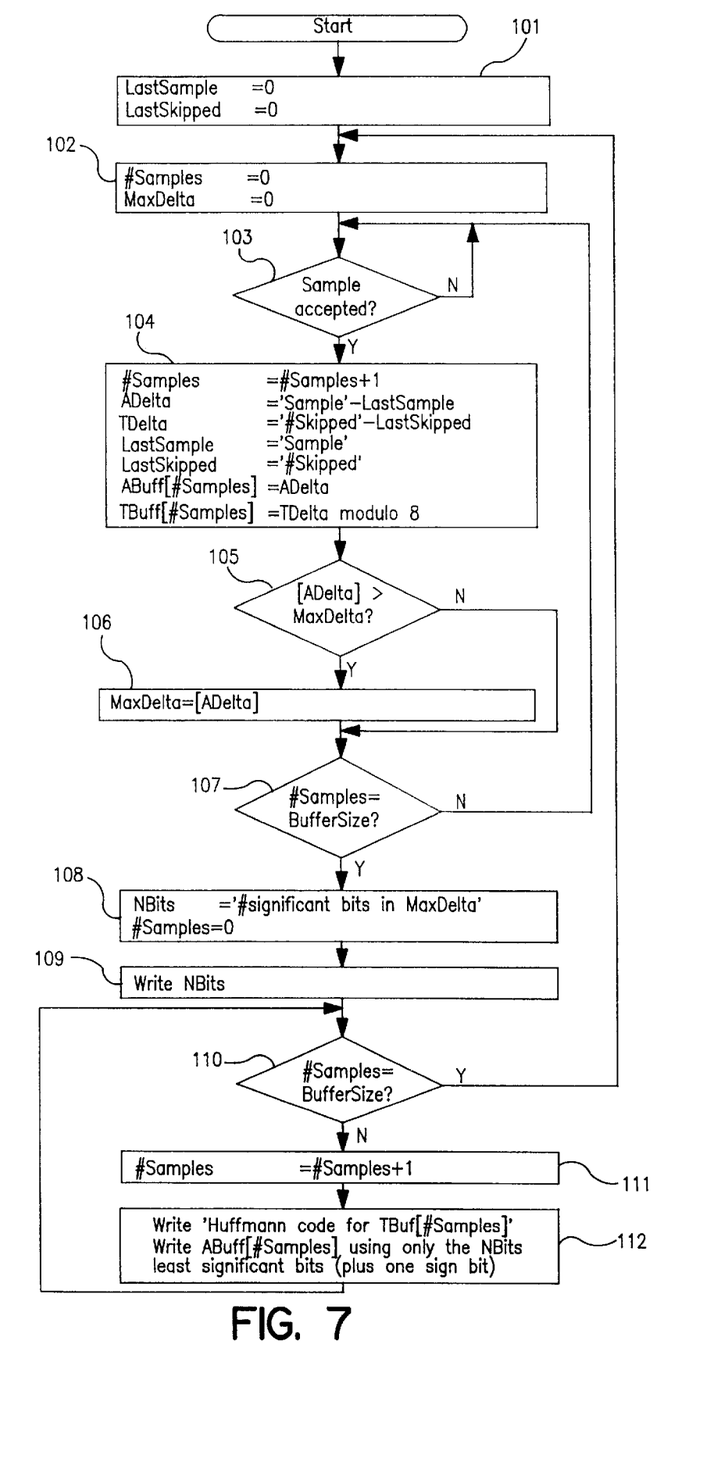
FIG. 7 is a flow diagram of an algorithm in accordance with this invention for compression of non-linear sample data, achieving the advantages of both non-linear sampling and data compression.

Referring now to FIG. 7, there is shown a complete compression algorithm for processing of non-linear sampled signals. At 101, the variables LastSample and LastSkipped are set equal to 0. At steps 101–107 a block of non-linear sample data is assembled in a manner similar to the lossless compression method, and the maximum absolute MaxDelta is determined as seen at step 106. The non-linear sampling, done in a circuit as illustrated in FIG. 6A, is indicated at 103. Looking at block 104, the primary difference compared to the original method as set forth in FIG. 3, is that the deltas representing the difference between sample amplitude values, ADelta, are stored in an amplitude buffer designated ABuf, while the deltas between the lapsed times, TDelta, are stored (modulo 8) in a time buffer Tbuf. During the compression phase, at blocks 108–112, the number of significant bits in MaxDelta is determined and this NBits value is written as a block header at 109. Next, all of the data representing sample time intervals in amplitude values is written at steps 110, 111 and 112. Thus, if the #Samples is not yet equal to BufferSize, as determined at 110, #Samples is incremented by 1 at step 111. Then, the Huffman code for the delta (# Skipped Samples) modulo 8 is written first, followed by the NBits least significant bits of the amplitude delta plus the sign bit). #Samples is then compared against BufferSize, incremented by 1, and the writing continues until all of the time and amplitude data for the block has been written, at which point the routine exits from 110 and goes back to 102, to work on the next block of data.

For retrieval of the data block, the value of NBits is read first. Next, all samples, consisting of both the time and amplitude information, is retrieved. The time information is retrieved by reading bit by bit and traversing through the Huffman code tree until a leaf node is reached. The contents of the leaf node is the decompressed delta (# Skipped Samples) modulo 8 parameter. Adding this value to the lapsed time of the previous sample, and again taking the modulo 8 value, results in the lapsed time for the current sample. The amplitude information is retrieved by reading sign bit and NBits least significant bits for the current delta and adding this to the amplitude of the previous sample. Finally, the entire signal is produced by reconstructing the discarded samples through interpolation of the retrieved samples. By this technique, the data produced by the non-linear sampling A/D converter is further compressed by about 25%, thus achieving an overall compression of 4:1 to 5:1 compared to the original signals.

While the invention has been disclosed in the context of cardiac and other physiological signals, it is to be noted that the invention is not limited to such physiological signals, but is applicable to sensor signals and other signals from quite different application areas, e.g., meteorology, seismology, etc. Particularly in battery-powered device environments, the system of the invention is quite usable for providing a very high degree of compression with relatively little loss. The non-linear sampling A/D converter of this invention not only saves energy during the digitization process, but also for any successive item in a processing chain. It is to be further noted that the non-linear sampling may be done in a digital embodiment, and is not limited to the analog embodiment disclosed.

We claim:

1. A system of non-linear sampling of an analog signal for obtaining compressed digital data representative of said analog signal, comprising:

a source for producing sample clock signals at a predetermined rate;

sampling means for sampling said analog signal with clock signals to obtain digital representations of said analog signal;

holding means for holding each sampled value of said analog signal;

threshold means for generating, upon each sampling of said analog signal, a difference threshold signal representing a dynamically decreasing difference with respect to said held sampled value;

sample accept means for determining at each sample clock following a said sampling whether the difference between said analog signal and said held sample value is more than said threshold value, and for generating an accept signal when said difference is greater; time means for determining the number of skipped samples between each said sampling and for generating a digital representation of said skipped samples; and enabling means for enabling said sample means to sample said analog signal with a said clock signal only when a said accept signal is generated, whereby some samples are skipped and sampling is done at a non-linear rate with a reduction of samples depending upon time differences in said analog signal and the shape of decrease of said threshold signal.

2. The system as described in claim 1, comprising storage means for storing in relation to each other for each sample the digital representation of said analog signal and the digital representation of lapsed time.

3. The system as described in claim 1, wherein said threshold means comprises means for generating a signal which starts at a predetermined magnitude and decreases to substantially zero within a predetermined time corresponding to a predetermined number of sample clocks following the last sampling.

4. A compression system for adapting the effective sampling rate of an analog signal as a function of variations of said analog signal, comprising:

sampling means for sampling said analog signal at a predetermined sampling rate;

block means for holding a selected number of said samples;

delta means for determining a delta value for each said held sample, said delta value being representative of the difference between each said sample and the prior sample;

max means, for determining for each said block, the maximum delta value of said block;

threshold means for setting a plurality of thresholds corresponding to predetermined different delta values;

comparison means for comparing said maximum value with said thresholds and, on the basis of said comparing, keeping some of said delta values and discarding the others; and writing means for writing compressed data made up of said maximum value and said kept delta values for each said block, wherein said threshold means comprises means for storing a plurality of respective discrete threshold values, and said comparison means comprises means for determining which two of said threshold values said maximum delta value is between, and for discarding delta values as a function of said determining.

5. The system as described in claim 4, wherein said writing means comprises telemetry means for direct telemetering of said compressed data.

6. The system as described in claim 4, wherein said writing means comprises storage means for storing said compressed data.

7. The system as described in claim 4, wherein said writing means has bit means for determining a number of bits for writing each kept delta value as a function of said determining.

8. The system as described in claim 4, wherein said system is housed in a pacemaker, and further comprising marker means for writing pacemaker marker data in said compressed data when a marker event has occurred during a said block.

9. An implantable pacemaker system, said system having pacing means for pacing a patient, sensing means for sensing physiologic analog signals, and data means for deriving from said analog signals compressed digital data representative of said analog signals, said data means comprising:

variation means for determining a measure of the variation of said analog signal;

non-linear means for obtaining sample data from said analog signal at a non-linear sample rate, said non-linear means comprising means for determining said non-linear sample rate as a function of said variation measure; and writing means for writing data representative of said non-linear rate and said obtained samples, wherein said non-linear means comprises clock means for generating clock signals, sample means for sampling said analog signals coincident with clock signals, converter means for converting samples into digital data, and sample skip means for causing said sample means to skip sampling corresponding to Portions of said analog signals which contain reduced variations with respect to said variation measure, whereby the number of sampling operations is reduced to less than the number of said sample clocks further comprising means for obtaining data representative of said skipped samples, and skip compression means for compressing said skipped sample data.

10. The system as described in claim 9, wherein said skip compression means comprises delta means for obtaining skip delta data representative of the difference between each successive sample pair of skipped samples between the pair samples.

11. The system as described in claim 9, comprising lossless compression means for compressing said sample digital data and code means for coding said skip delta data.

12. A method of obtaining a compressed data representation of an analog signal, comprising:

establishing threshold data relating to anticipated values of said analog signal;

sampling said analog signal at an effective non-linear rate to obtain non-linear sample data, said non-linear sampling including comparing said analog signal to said threshold data and deriving said non-linear rate from said comparing;

obtaining a measure of said non-linear rate corresponding to each sample, and converting said measures into rate data;

losslessly compressing said sample data establishing discrete threshold data points, first sampling said analog signal at a fixed rate to obtain first sample data, comparing said first sample data with said threshold data points, and non-linear sampling said first sample data as a function of said comparison; and writing said rate data and said sample data.

13. The method as described in claim 12, comprising establishing analog threshold data, and deriving said non-linear rate before sampling said analog signal.

14. The method as described in claim 12, comprising generating sample clocks at a predetermined clock rate, for each said clock determining whether to skip a sample or take a sample, and obtaining said non-linear rate measure by determining skipped samples.

15. The method as described in claim 14, comprising compressing said rate data by determining the differences of skipped samples between successive samples, and coding said differences.

16. An implantable medical device system comprising:

comprising a pacemaker, said pacemaker having marker means for obtaining marker channel data, signal means for obtaining an analog physiological signal; and data means for obtaining a compressed digital data stream representative of said analog signal, said data means having non-linear means for obtaining non-linearly spaced samples of said analog signal, first compression means for providing compressed data representative of said samples, and second compression means for providing compressed data representative of the spacing of said samples, thereby providing a data stream representative of said analog signal and insertion means for inserting said marker channel data into said data stream.

17. The system as described in claim 16, wherein said non-linear means comprises an analog non-linear sampling A/D converter which determines sampling rate before A/D conversion.

18. The system as described in claim 16, wherein said non-linear means comprises A/D sampling means for obtaining digital samples representative of said analog signal, and sample-skipping means for skipping some of said digital samples as a function of the rate of variation of said analog signal.

19. The system as describe in claim 16, wherein said non-linear means comprises threshold signal means for generating a threshold signal, said threshold signal being initialled upon each said sample.

20. The system as described in claim 19, comprising clock means for generating clock signals and comparator means operative at each said clock signal for comparing said threshold signal with said analog signal.

21. The system as described in claim 19, comprising means for adjusting said threshold signal as a function of signal history.

22. The system as described in claim 19, comprising program means for adjusting said threshold signal as a function of programmed data.

23. The system as described in claim 19, wherein said threshold signal has an initial value and a length, and adjusting means for adjusting either of said initial value and length.

24. The system as described in claim 23, wherein said adjusting means comprises accumulating means for accumulating data representative of said analog signal and for adjusting said threshold signal as a function of said accumulated data.

* * * * *